(12) United States Patent
Sugito et al.

(10) Patent No.: US 7,309,332 B2
(45) Date of Patent: Dec. 18, 2007

(54) WEARING ARTICLE

(75) Inventors: Tomoko Sugito, Kagawa-ken (JP);
Yoshitaka Mishima, Kagawa-ken (JP);
Kaiyo Nakajima, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 231 days.

(21) Appl. No.: 10/688,096

(22) Filed: Oct. 17, 2003

(65) Prior Publication Data

US 2004/0153043 A1      Aug. 5, 2004

(30) Foreign Application Priority Data

Oct. 17, 2002   (JP)   ............... 2002-303080

(51) Int. Cl.
*A61F 13/15*   (2006.01)
(52) U.S. Cl. ............... 604/385.25; 604/385.24; 604/385.29; 604/385.27
(58) Field of Classification Search ........... 604/385.24, 604/385.25, 385.29, 385.27
See application file for complete search history.

(56) References Cited

U.S. PATENT DOCUMENTS

| 4,355,425 | A |   | 10/1982 | Jones et al. |
|---|---|---|---|---|
| 4,897,084 | A |   | 1/1990 | Ternstroem et al. |
| 5,447,508 | A | * | 9/1995 | Numano et al. ........ 604/385.27 |
| 6,179,820 | B1 |   | 1/2001 | Fernfors |
| 6,440,116 | B1 |   | 8/2002 | Tanji et al. |
| 6,482,195 | B1 | * | 11/2002 | Kumasaka ............. 604/385.27 |

FOREIGN PATENT DOCUMENTS

| EP | 0 073 183 | 3/1983 |
|---|---|---|
| EP | 1 080 708 | 3/2001 |
| EP | 1 132 070 | 9/2001 |
| EP | 1 201 212 | 5/2002 |
| EP | 1 243 237 | 9/2002 |
| EP | 1 297 809 | 4/2003 |
| EP | 1 374 815 | 1/2004 |
| GB | 2 282 522 | 4/1995 |
| WO | WO 01 74280 | 10/2001 |

* cited by examiner

*Primary Examiner*—Jacqueline F. Stephens
(74) *Attorney, Agent, or Firm*—Butzel Long

(57) ABSTRACT

Here is disclosed a wearing article made of an elastically stretchable chassis defining a front waist region, a rear waist region and a crotch region. This sheet is composed of a first elastic segment extending, substantially in parallel to peripheral portions destined to form leg-holes, from a transversely middle zone of the crotch region to lateral portions of the front and rear waist regions, and a second elastic segment defined by the remaining portion except for the first elastic segment wherein the first elastic segment has a stretch stress higher than that of the second elastic segment.

10 Claims, 7 Drawing Sheets

WEARING ARTICLE

BACKGROUND OF THE INVENTION

The present invention relates to a wearing article suitable for a disposable diaper, pants for an incontinent patient, sanitary shorts or the like.

The disposable diaper provided in its crotch region with a depression adapted to receive feces is well known. For example, Japanese Utility Model Registration No. 2523711B (DOCUMENT 1) discloses the disposable diaper formed around the feces receiving depression with a flexible protrusion.

Japanese Publication of Translated version No. 1997-504194A (DOCUMENT 2) discloses the sanitary pants provided with elastic means (elastic member) extending over its crotch region further to respective edges of the front and rear waist regions in the longitudinal direction of the sanitary pants so that the absorbent core may be tightly placed against the wearer's body as the elastic means contract.

However, the disposable diaper provided with the protrusion disclosed by above-cited DOCUMENT 1 has the problem left behind how this protrusion can be placed in tight contact with the wearer's body. The sanitary pants disclosed by above-cited DOCUMENT 2 is accompanied with the inconvenience that the contractile force of the elastic means certainly functions to place the absorbent core closely against the wearer's body but simultaneously functions to pull the waist surrounding end portion of the pants downward.

SUMMARY OF THE INVENTION

It is an object of the present invention to provide a wearing article improved to overcome these problem and inconvenience.

According to the present invention, there is provided a wearing article comprising an elastically stretchable chassis having a front waist region, a rear waist region and a crotch region extending therebetween.

The chassis is composed of a first elastic segment extending substantially along peripheral portions forming leg-holes, from a transversely middle zone of the crotch region to the lateral portions of the front and rear waist regions and a second elastic segment defined by a remaining portion of the chassis except for the first elastic segment wherein the first elastic segment has a stretch stress higher than that of the second elastic segment.

The present invention includes the following embodiments.

(1) The lateral portions of the front and rear waist regions are releasably engaged with each other to define the waist-hole and the leg-holes.

(2) The lateral portions of the front and rear waist regions are permanently joined together to define the waist-hole and the leg-holes.

(3) The transversely middle zone of the crotch region is formed on its inner side with an annular protrusion adapted to surround at least one of anus and urethral of a wearer and the first elastic segment extends along the leg-surrounding peripheral portions from the annular protrusion to the respective lateral portions of the front and rear waist regions.

(4) The first elastic segments formed in the front and rear waist regions become contiguous to each other on the lateral portions of the front and rear waist regions as the front and rear waist regions are joined together along the lateral portions of the waist regions.

(5) The wearing article is one of an open-type disposable diaper, a pull-on disposable diaper, a diaper cover and sanitary shorts.

(6) The chassis is provided along at least one of a waist-hole's peripheral portion and leg-holes' peripheral portions with an elastic member or elastic members extending outside the first elastic segment along the peripheral portion or portions.

(7) The first elastic segment exhibits a stretch stress of 0.25 N/width of 15 mm or higher at a stretch ratio of 15% and a stretch stress of 0.6 N/width of 15 mm at a stretch ratio of 40% and the stretch stress of the first elastic segment is at least 1.5 times of the stretch stress of the second elastic segment.

(8) The second elastic segment comprises at least a single elastic sheet extending over the front and rear waist region and the crotch region and the first elastic segment is formed by overlaying and joined an elastic sheet to the single elastic sheet forming the second elastic segment.

(7) The elastic sheet to be overlaid and joined to the single elastic sheet forming the second elastic segment comprises a pair of sheets extending from the transversely middle zone of the crotch region substantially along the leg-holes' peripheral portions to the lateral portions of the front and rear waist regions, respectively, and describing substantially circular arcs which are convex inward in a transverse direction wherein the pair of sheets are overlapped and joined together in the middle zone of the crotch region.

DETAILED DESCRIPTION OF THE PREFERRED EMBODIMENTS

Details of the wearing article according to the present invention will be more fully understood from the description of the disposable diaper as a specific embodiment of the invention given hereunder with reference to the accompanying drawings.

Figure 1:
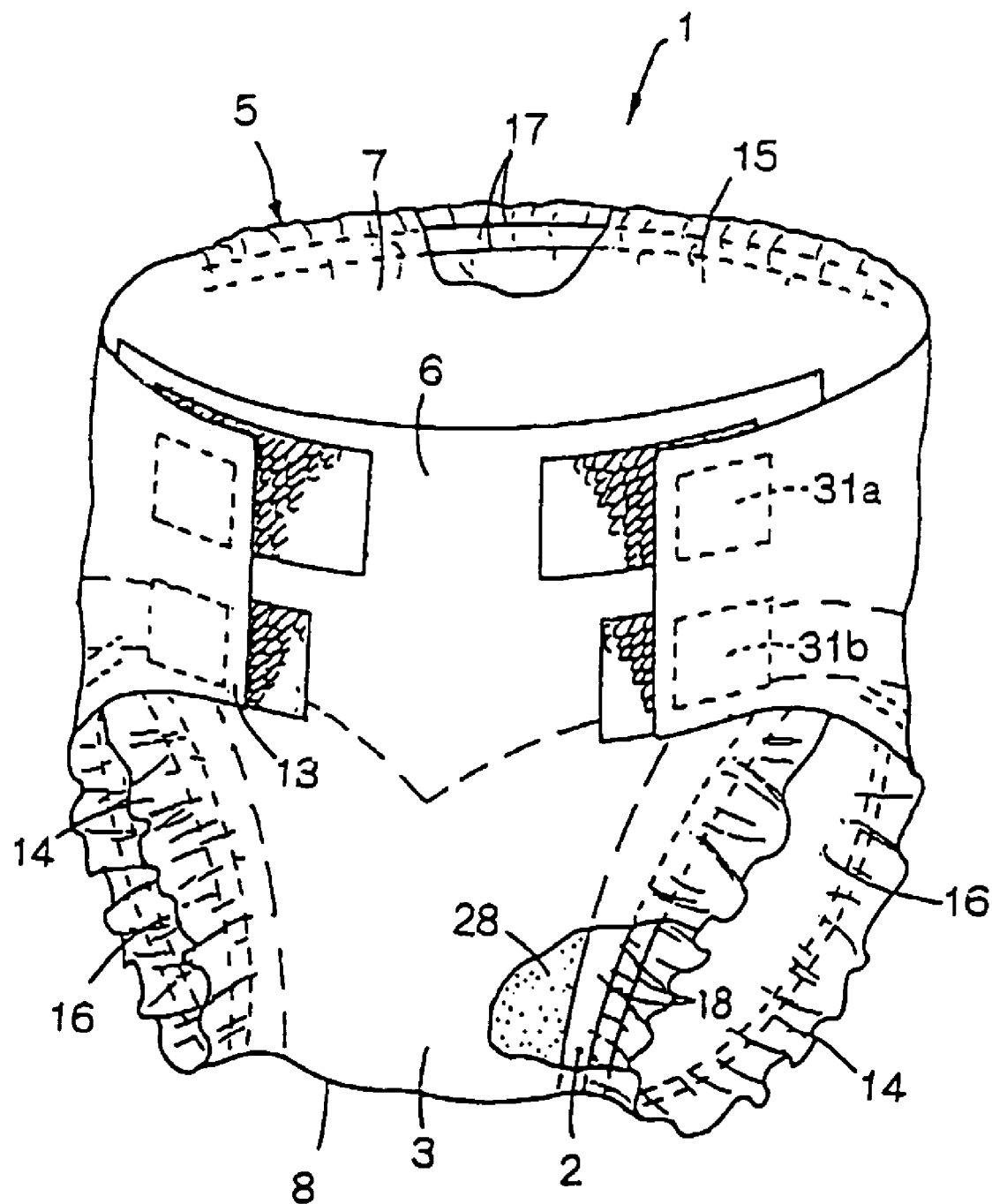
FIG. 1 is a perspective view of a disposable diaper as a typical embodiment of the invention.
Figure 2:
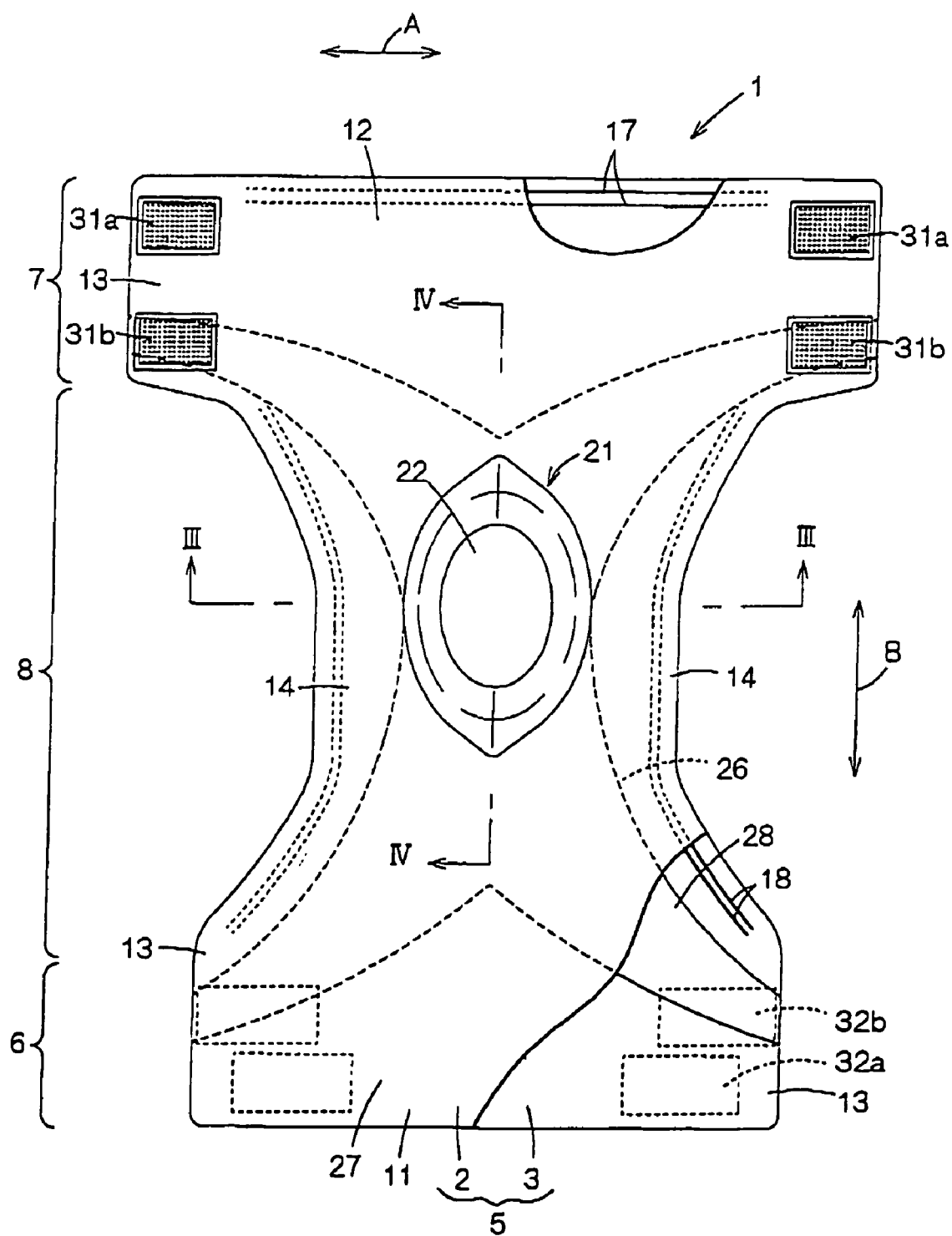
FIG. 2 is a partially cutaway plan view showing the diaper of FIG. 1.

FIG. 1 is a perspective view of a disposable diaper 1 as put on a wearer's body and FIG. 2 is a partially cutaway plan view showing this diaper. This diaper 1 is of open-type having a waist-hole 15 and a pair of leg-holes 16 formed as the diaper is put on the wearer's body. The diaper 1 has a transverse direction indicated by a double-headed arrow A and a longitudinal direction indicated by a double-headed arrow B in the plan view. The diaper 1 presenting an hourglass-shape in its developed plan view includes a chassis 5 which is elastically stretchable in the transverse direction A as well as in the longitudinal direction B. The chassis 5 comprises an elastically stretchable topsheet 2 destined to come in contact with the wearer's body and an elastically stretchable backsheet 3 destined to come in contact with a wearer's garment, wherein these two sheets 2, 3 are intermittently joined together by use of an adhesive or a suitable welding technique. The diaper 1 is composed of, in the longitudinal direction B, a front waist region 6, a rear waist region 7 and a crotch region 8 extending between the front and rear waist regions 6, 7. The diaper 1 is substantially contoured by front and rear end portions 11, 12 extending in the transverse direction A and transversely opposite lateral portions 13 extending in the longitudinal direction B wherein these lateral portions 13 curve inward, in the crotch region 8, to define leg-surrounding lateral portions 14. Along the rear end portion 12 and the leg-surrounding lateral portions 14, a waist-surrounding elastic members 17 each comprising a plurality or rubber threads and leg-surrounding elastic members 18 each comprising a plurality of rubber threads are interposed between the topsheet 2 and the backsheet 3 and bonded to at least one of these two sheets 2, 3 in a stretched or unstretched state. In a transversely middle zone of the crotch region 8, the diaper 1 is formed on its inner side with an annular protrusion 21 so that a space surrounded by this annular protrusion 21 may define a feces receiving pocket 22. This protrusion 21 is formed at a location in the crotch region 8 put aside toward the rear waist region 7 so that the protrusion 21 may come in contact with the wearer's body around the anus as the diaper 1 is put on the wearer's body.

The chassis 5 in the diaper 1 formed in this manner comprises, as seen in FIG. 2, a zonal high elasticity segment 26 extending from the periphery of the annular protrusion 21 toward the lateral portions 13 in the front waist region 6 as well as toward the lateral portions 13 in the rear waist region 7 so as to describe a substantially X-like shape and a low elasticity segment 27 defined by the remaining segment of the chassis 5. When the diaper 1 is put on the wearer's body, a higher stretching force is necessary for the high elasticity segment 26 than a stretching force necessary for the low elasticity segment 27. The high elasticity segment 26 extends along the respective leg-surrounding lateral portions 14.

Such high elasticity segment 26 is formed by an elastically stretchable sheet 28 interposed between the top- and backsheets 2, 3 and bonded to at least one of these sheets 2, 3. This elastic sheet 28 preferably has a stretch stress equal to or higher than those of the top- and backsheets 2, 3. It should be understood that the waist-surrounding elastic member 17 as well as the leg-surrounding elastic members 18 are optionally used to assist the chassis 5 to be closely placed around the wearer's waist and thighs and the diaper 1 may be made without one or both of these elastic members 17, 18.

In the preferred chassis 5, the high elasticity segment 26 has a stretch stress of 0.25 N/15 mm or higher when the segment 26 is transversely stretched by 15% and a stretch stress of 0.6 N/15 mm when the segment 26 is transversely stretched by 40%. At these stretch ratios, the high elasticity segment 26 exhibits the stretch stress corresponding to at least 1.5 times of the stretch stress exhibited by the low elasticity segment 27.

The diaper 1 further comprises fastener means. Specifically, each of the opposite lateral portions 13 in the rear waist region 7 is provided with a pair of hook members 31a, 31b attached to the topsheet 2 each making one cooperating component of the mechanical fastener commonly known in the trade name of MAGIC TAPE, on one hand, and each of the opposite lateral portions 13 in the front waist region 6 is provided with a pair of loop members 32a, 32b attached to the backsheet 3 each making the other cooperating component of the mechanical fastener, on the other hand. Of these mechanical fastener components, at least the hook members 31b and the loop members 32b at least partially overlap the high elasticity segment 26.

Figure 3:
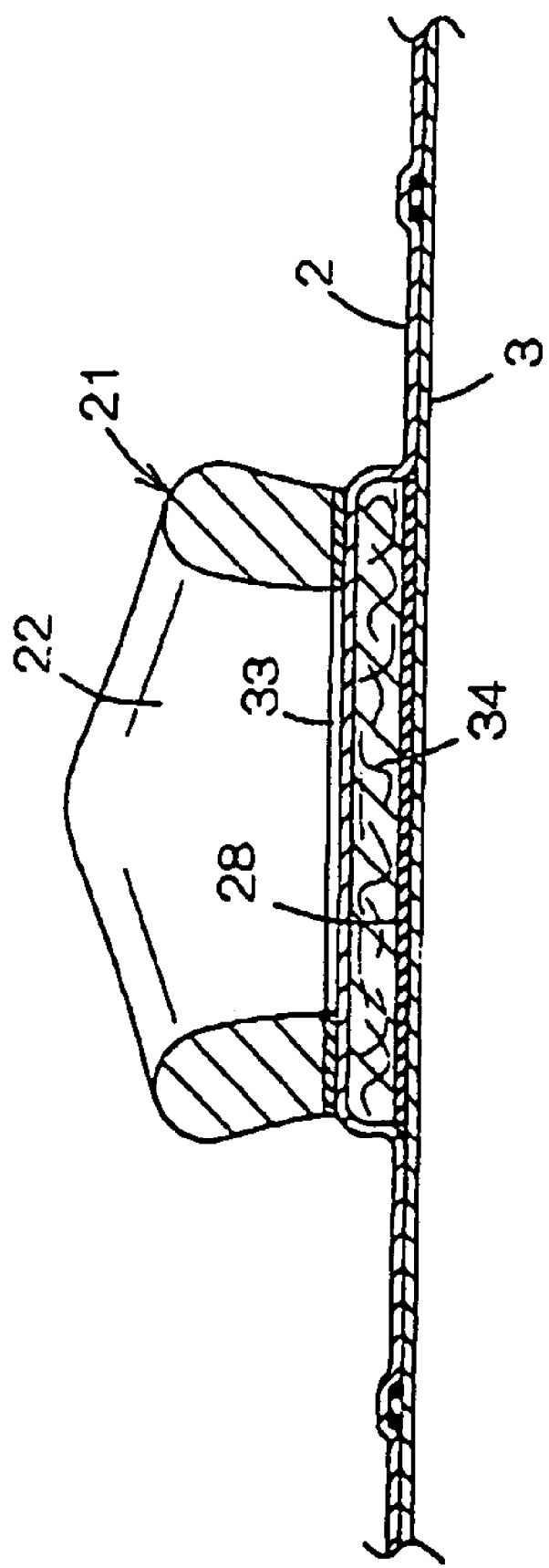
FIG. 3 is a partially cutaway sectional view taken along a line III-III in FIG. 2.
Figure 4:
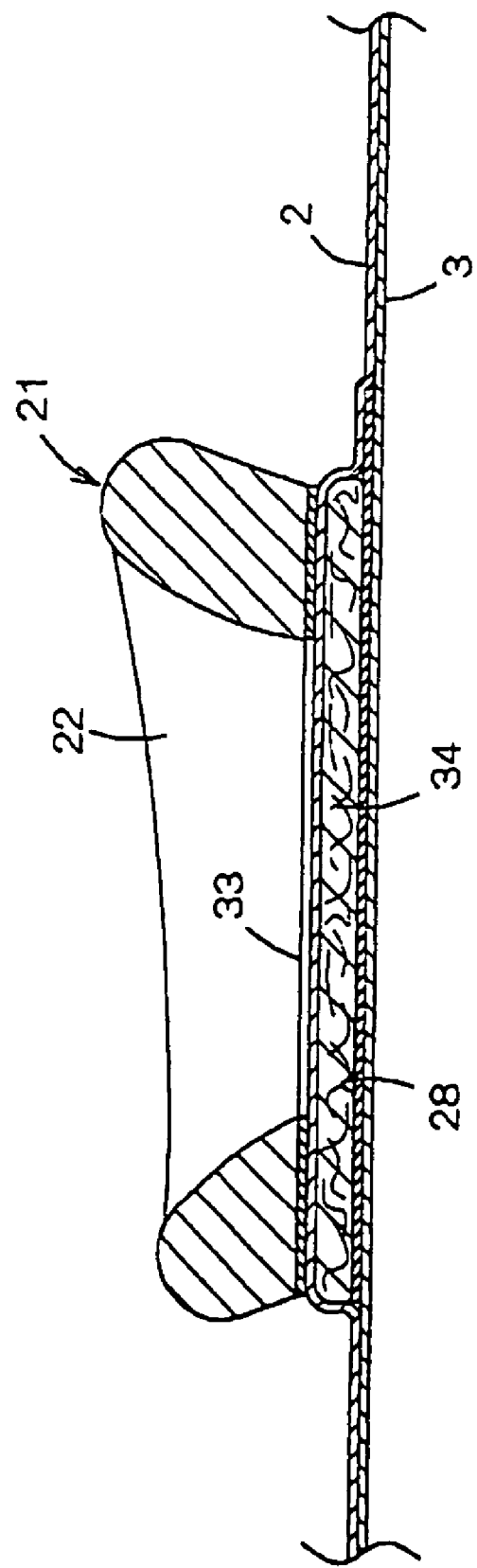
FIG. 4 is a partially cutaway sectional view taken along a line IV-IV in FIG. 2.

FIGS. 3 and 4 are partially sectional views taken along lines III-III and IV-IV in FIG. 2, respectively. The protrusion 21 is formed by flexible foamed urethane rubber or the like and bonded to the topsheet 2 by means of an adhesive 33. A bottom of the feces receiving depression 22 is defined by the topsheet 2 which covers, in turn, a body fluid absorbent core 34 underlying the topsheet 2. The elastic sheet 28 and the backsheet 3 underlie the core 34 in this order.

The core 34 is formed by fluff pulp or a mixture of fluff pulp and super-absorbent polymer particles. The topsheet 2 is liquid-pervious at least in its zone covering the core 34 and the backsheet 3 is liquid-impervious at least in its zone underlying the core 34.

To put the diaper 1 formed in the manner as has been described above on the wearer's body, the protrusion 21 is placed against the wearer's body so that the protrusion 21 may surround the wearer's anus, then the lateral portions 13 of the rear waist region 7 are placed upon the lateral portions 13 of the front waist region 6 and finally the lateral portions 13 of the rear waist region 7 are pulled in a waist-circumferential direction to engage the hook members 31a, 31b with the associated loop members 32a, 32b. Thereupon the high elasticity segment 26 extending to the respective lateral portions 13 of the front and rear waist regions 6, 7 are overlapped with itself in the respective lateral portions 13 so as to form loops surrounding the wearer's thighs. In this state, the high elasticity segment 26 having high stretch stress functions to press the protrusion 21 against the wearer's body. There is no anxiety that the protrusion 21 might shift off from its desired position and/or might be spaced from the wearer's body, so discharged feces, particularly loose passage can be reliably received by the feces receiving depression 22 and retained therein without any apprehension that such bodily discharges might leak out beyond the protrusion 21. A tensile force of the high elasticity segment 26 generated when the diaper 1 is put on the wearer's body principally acts upon a zone defined between the crotch region 8 and the waist's lateral portions 13 but substantially not upon the front and rear end portions 11, 12 defining together the waist-hole. Consequently, the diaper 1 is free from the inconvenience that the diaper 1 might slip down, particularly in the vicinity of the waist-hole, under the effect of the tensile force of the high elasticity segment 26.

Figure 5:
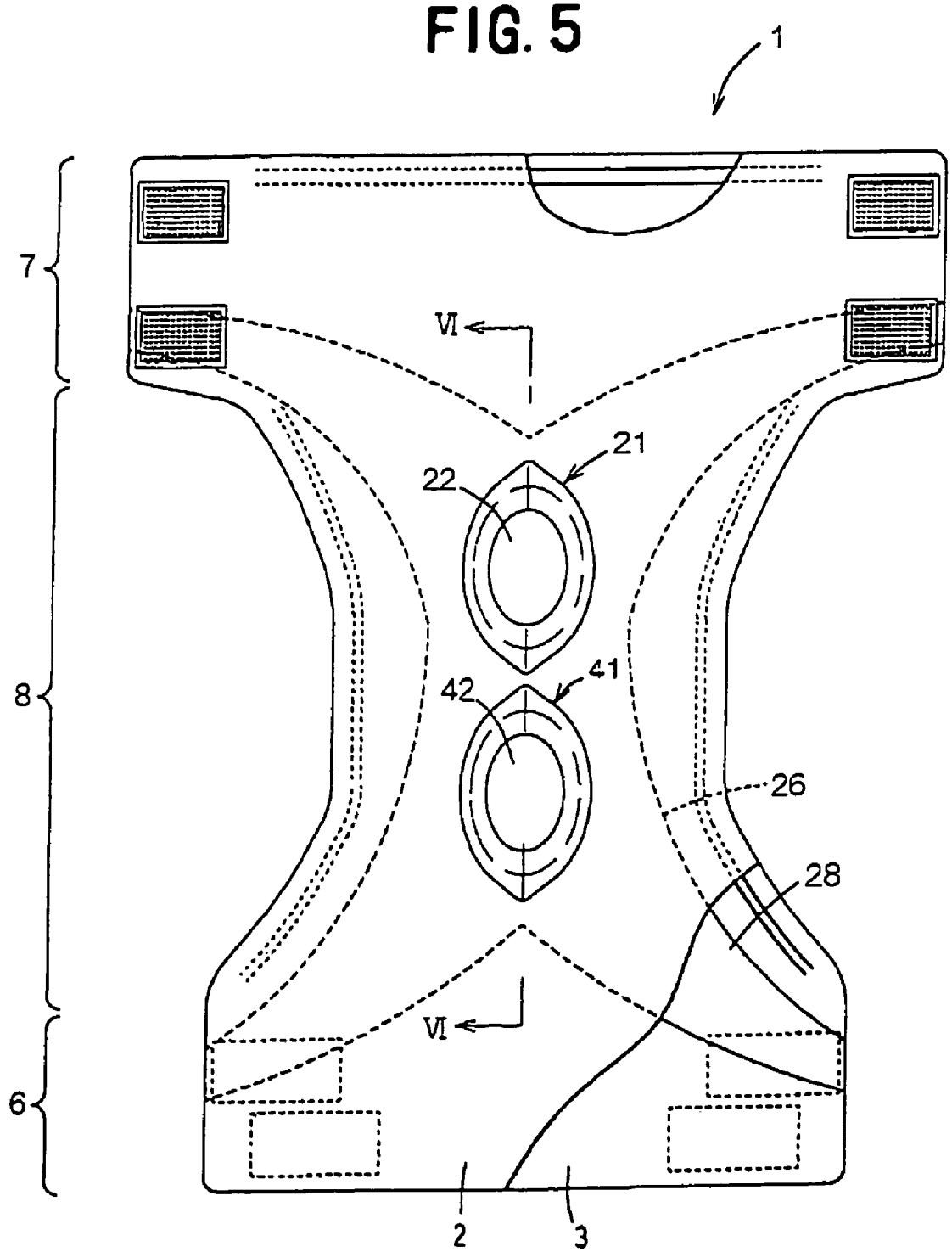
FIG. 5 is a view similar to FIG. 2 showing another embodiment of the invention.
Figure 6:
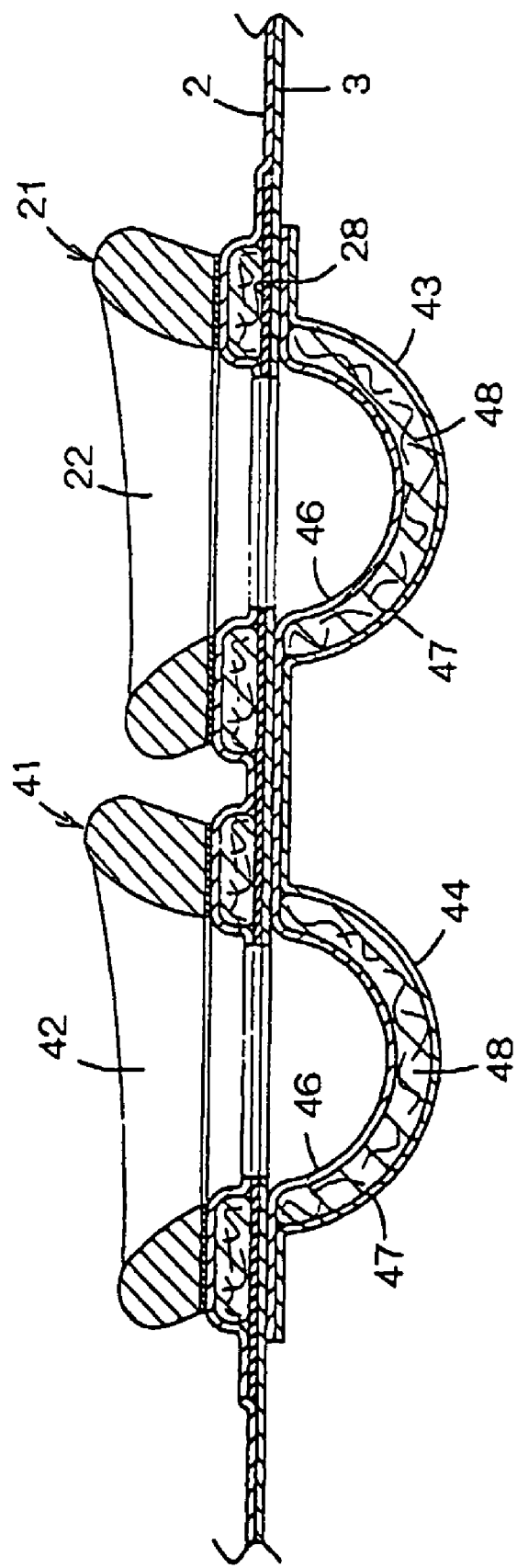
FIG. 6 is a partially sectional view taken along a line VI-VI in FIG. 5.

FIG. 5 is a view similar to FIG. 2 showing another embodiment of the invention and FIG. 6 is a partially sectional view taken along a line VI-VI in FIG. 5. The diaper 1 according to this embodiment has a first protrusion 21 and a feces receiving depression 22 similar to those in the embodiment shown in FIG. 2 and additionally has an annular second protrusion 41 at a location in the crotch region 8 put aside toward the front waist region 6 so as to define a urine receiving depression 42 inside the second annular protrusion 41. A high elasticity segment 26 comprising top- and backsheets 2, 3 and an elastic sheet 28 extends so as to pass under the first and second protrusions 21, 41 and to describe X-shape. The feces receiving depression 22 and the urine receiving depression 42 have respective bottoms 43, 44 comprising a liquid-pervious sheet 46, a liquid-impervious sheet 47 and a body fluid absorbent core 48 interposed between these two sheets 46, 47. These bottoms 43, 44 bulge outwardly of the diaper 1 in bag-like shape. The diaper 1 according to this embodiment ensures the first protrusion 21 to be tightly placed against the wearer's body around the anus and at the same time ensures the second protrusion 41 to be tightly placed against the wearer's body around the urethral.

It is possible without departing from the scope of the invention to bond the elastic sheet 28 to the upper surface of the topsheet 2 or the lower surface of the backsheet 3 as viewed in FIG. 3 instead of interposing the elastic sheet 28 between the top- and backsheets 2, 3. It is also possible to implement the present invention in the form of the article having the urine receiving depression 42 alone but not the feces receiving depression 22. The present invention is not limited to the open-type diaper as illustrated but applicable also to a pull-on diaper in which the lateral portions 13 of the front waist region 6 as well as the lateral portions 13 of the rear waist region 7 are overlaid and joined together. In the course of bonding the lateral portions 13, zones of the high elasticity segment 26 extending in the front and rear waist regions 6, 7 are preferably overlapped each other and substantially contiguous to each other. Between the top- and backsheets 2, 3, it is possible to interpose a core which is larger than both the core 34 and the core 48 in illustrated embodiments. Preferably, the cores 34, 48 are intermittently bonded to only one of the top- and backsheets 2, 3 in order to prevent extensibilities of these top- and backsheets 2, 3 from being deteriorated.

Figure 7:
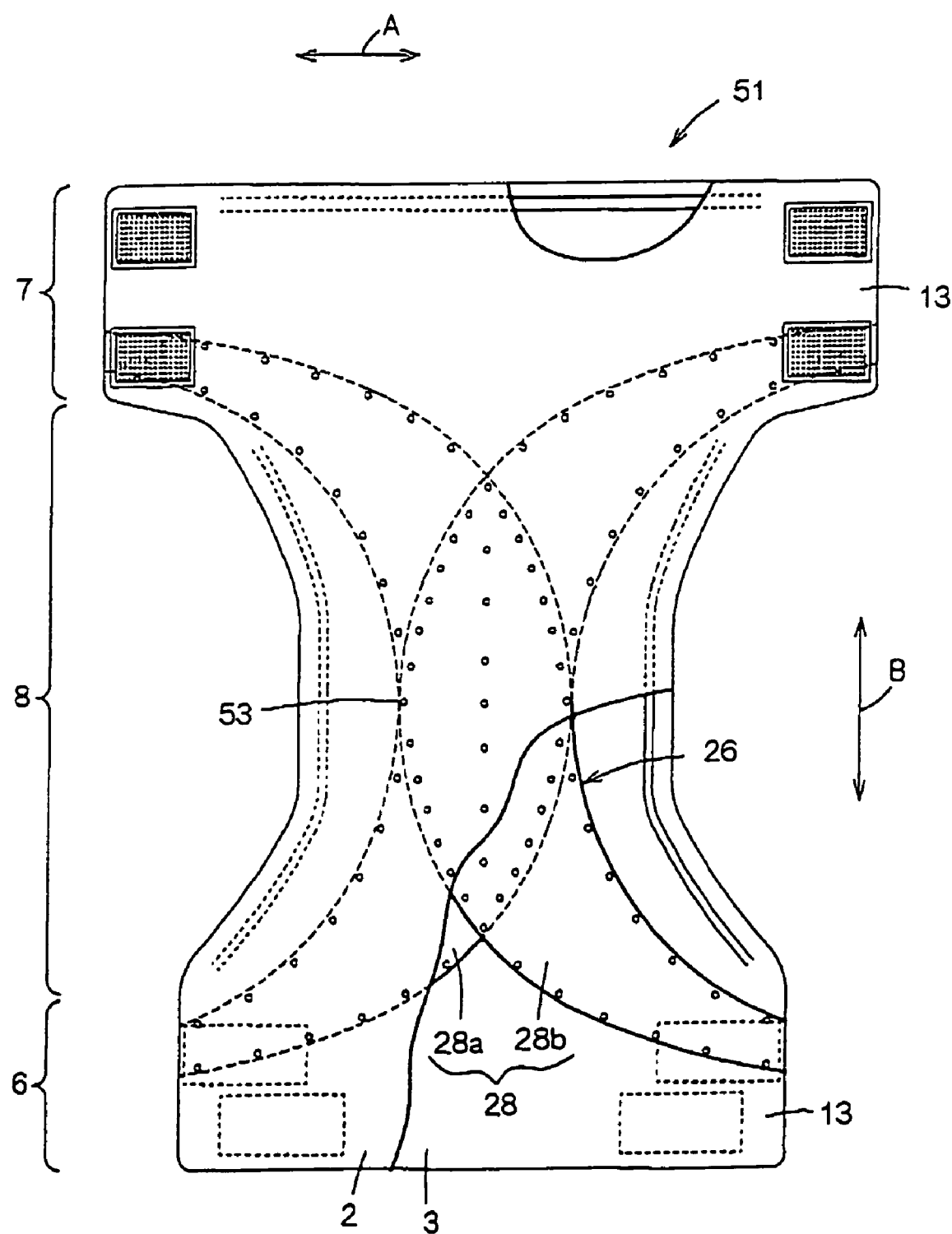
FIG. 7 is a view similar to FIG. 2 showing still another embodiment of the invention.

FIG. 7 is a view similar to FIG. 2 showing still another embodiment of the invention. A wearing article 51 according to this embodiment has neither the annular protrusion 21 nor the absorbent core 34 both seen in FIG. 2 and is suitable for use as covering means, for example, diaper cover used to hold a urine-absorbent pad (not shown) in tight contact with the wearer's crotch region. This wearing article 51 is different from the embodiment shown in FIG. 2 in that the elastic sheet 28 forming the high elasticity segment 26 comprises a pair of elastically stretchable sheets 28a, 28b extending substantially parallel to the leg-surrounding lateral portions 14 from a central zone of the crotch region 8 to the lateral portions 13 in the front and rear waist regions 6, 7 and describing substantially circular arcs which are convex inward in a width direction A. These elastic sheets 28a, 28b are overlapped and joined together by means of an adhesive or welding techniques in the central zone of the crotch region 8. As a stock material for these elastic sheets 28a, 28b, it is possible to use the same sheet material as one of the top- and backsheets 2, 3 or the sheet material having a stretch stress higher than those of the top- and backsheets 2, 3. In the central zone of the crotch region 8, the top- and backsheets 2, 3 may be placed upon and bonded to the elastic sheets 28a, 28b to maximize a stretch stress in this central zone generated as the wearing article 51 is stretched in the transverse direction A and in the longitudinal direction B. The wearing article 51 shown in FIG. 7 has a plurality of weld spots 53 at which the sheets placed one upon another are welded together. Extensibility of the elastic sheets 28a, 28b can be controlled by the number of these spots 53 per unit area or the layout of spot distribution. Referring to FIG. 7, the spots 53 are distributed most densely in the crotch region 8.

In the case of such wearing article 51, the high elasticity segment 26, particularly the central zone of the crotch region 8 ensures the disposable diaper or the urine-absorbent pad set on the inner side of the wearing article 51 to be tightly held in contact with the wearer's crotch region. The wearing article 51 may be folded in the longitudinal direction B with the topsheet 2 inside and then the lateral portions 13 put flat together may be joined together to obtain the pull-on wearing article 51. This wearing article 51 is suitable also as sanitary shorts used to hold a sanitary napkin in close contact with the wearer's body.

With the wearing article according to the present invention, the high elasticity segment extends from the central zone of the crotch region to the lateral portions of the front waist region and to the lateral portions of the rear waist region so as to describe a substantially X-like shape. Under the effect of this high elasticity segment, the central zone of the crotch region reliably holds the annular protrusion defining the feces receiving depression formed in this zone of the wearing article or a disposable diaper, a urine absorbent pad or a sanitary napkin set in this zone of the wearing article in close contact with the wearer's body. In addition, there is no anxiety that the wearing article might slid down along the wearer's waist due to the effect of this high elasticity segment.

What is claimed is:

1. A wearing article comprising: an elastically stretchable chassis having a front waist region, a rear waist region and a crotch region extending therebetween; and said chassis being composed of a first elastic segment extending substantially along peripheral portions forming leg-holes, from and across a transversely middle zone of said crotch region to lateral portions of said front and rear waist regions so that a transversely opposite inner edges of said first elastic segment have shapes that curve transversely outward from a longitudinal central portion to longitudinal opposite ends of said first elastic segment, and a second elastic segment defined by a remaining portion of said chassis which consists of the entire chassis excusive of said first elastic segment wherein said first elastic segment has a stretch stress higher than that of said second elastic segment.

2. The wearing article according to claim 1, wherein said lateral portions of said front and rear waist regions are releasably engaged with each other to define said waist-hole and said leg-holes.

3. The wearing article according to claim 1, wherein said lateral portions of said front and rear waist regions are permanently joined together to define said waist-hole and said leg-holes.

4. The wearing article according to claim 1, wherein said transversely middle zone of said crotch region is formed on its inner side with an annular protrusion adapted to surround at least one of anus and urethral of a wearer and said first elastic segment extends along said leg-surrounding peripheral portions from said annular protrusion to the respective lateral portions of said front and rear waist regions, said annular protrusion extending upward from the crotch region and terminating at a free distal end.

5. The wearing article according to claim 1, wherein said first elastic segments formed in said front and rear waist regions become contiguous to each other on said lateral portions of said front and rear waist regions as said front and rear waist regions are joined together along said lateral portions of said waist regions.

6. The wearing article according to claim 1, wherein said wearing article is one of an open-type disposable diaper, a pull-on disposable diaper, a diaper cover and sanitary shorts.

7. The wearing article according to claim 1, wherein said chassis is provided along at least one of a waist-hole's peripheral portion and leg-holes' peripheral portions with an elastic member or elastic members extending outside said first elastic segment along said peripheral portion or portions.

8. The wearing article according to claim 1, wherein said first elastic segment exhibits a stretch stress of 0.25 N/width of 15 mm or higher at a stretch ratio of 15% and a stretch stress of 0.6 N/width of 15 mm at a stretch ratio of 40% and wherein the stretch stress of said first elastic segment is at least 1.5 times of the stretch stress of said second elastic segment.

9. The wearing article according to claim 1, wherein said second elastic segment comprises at least a single elastic sheet extending over said front and rear waist region and said crotch region and said first elastic segment is formed by overlying and joining an elastic sheet to said single elastic sheet forming said second elastic segment.

10. The wearing article according to claim 9, wherein said elastic sheet to be overlaid and joined to said single elastic sheet forming said second elastic segment comprises a pair of sheets extending from said transversely middle zone of said crutch region substantially along said leg-holes' peripheral portions to said lateral portions of said front and rear waist regions, respectively, and describing substantially circular arcs which are convex inward in a transverse direction and wherein said pair of sheets are overlapped and joined together in said middle zone of said crotch region.

* * * * *